United States Patent
Brown et al.

(10) Patent No.: US 6,348,065 B1
(45) Date of Patent: *Feb. 19, 2002

(54) LONGITUDINALLY FLEXIBLE EXPANDABLE STENT

(75) Inventors: Brian J. Brown, Hanover; Michael L. Davis, Shorewood, both of MN (US)

(73) Assignee: Scimed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,431

(22) Filed: Jul. 24, 1998

Related U.S. Application Data (63) Continuation of application No. 08/511,076, filed on Aug. 3, 1995, which is a continuation-in-part of application No. 08/396,569, filed on Mar. 1, 1995, now abandoned.

(51) Int. Cl.[7] .................................................. A61F 2/06

(52) U.S. Cl. ...................... 623/1.16; 606/198; 623/1.18

(58) Field of Search .............................. 623/1.15, 1.16, 623/1.17, 1.18, 1.19; 606/195, 198

(56) References Cited

U.S. PATENT DOCUMENTS

| | | |
|---|---|---|
| 2,836,181 A | 5/1958 | Tapp |
| 3,105,492 A | 10/1963 | Jeckel |
| 3,272,204 A | 9/1966 | Artandi et al. |
| 3,490,975 A | 1/1970 | Lightwood et al. |
| 3,509,883 A | 5/1970 | Dibelius |
| 3,526,228 A | 9/1970 | Lyng |
| 3,562,820 A | 2/1971 | Braun |

(List continued on next page.)

FOREIGN PATENT DOCUMENTS

| | | |
|---|---|---|
| EP | 0 364 787 B1 | 4/1990 |
| EP | 0 540 290 A2 | 5/1993 |
| EP | 0 541 443 A1 | 5/1993 |
| EP | 0 606 165 A1 | 7/1994 |
| JP | 6-4175 | 3/1994 |
| WO | WO 94/17754 | 8/1994 |

OTHER PUBLICATIONS

Manufacturing Processes for Engineering Materials, by Serope Kalpakjian, Illinois Institute of Technology, Addison–Wesley Publishing Company, pp. 340.

A View of Vascular Stents, by Richard A. Schatz, MD, From the Arizona Heart Institute Foundation, Phoenix, Arizona, *Circulation* , vol. 79, No. 2, Feb. 1989, pp. 445–457.

The Self–Expanding Mesh Stent, by Ulrich Sigwart, *Section IV*, Chapter 29, pp. 605–610.

Japanese Infringement Search on Articulated Expandable Stents, Dated Jul. 12, 1995.

*Engineering Fluid Mechanics, Third Edition* , John A. Roberson and Clayton T. Crowe, pp. 94 and pp. 414–421.

*Cambridge Dictionary of Science and Technology*, Cambridge University Pressp. 128.

(List continued on next page.)

*Primary Examiner*—Paul B. Prebilic
(74) *Attorney, Agent, or Firm*—Vidas, Arrett & Steinkraus (57) ABSTRACT

The invention provides a tubular expandable stent including a plurality of cylindrically shaped open cylindrical segments aligned on a common longitudinal axis to define a generally tubular stent body, each segment being defined by a member formed in an undulating flexible pattern of interconnected substantially parallel struts with pairs thereof having alternating interconnecting end portions to define the periphery of the expandable stent segment, and in which the connected end portions of paired struts in each segment, before the stent is expanded, are positioned substantially opposite to connected end portions of paired struts in adjacent segments.

45 Claims, 5 Drawing Sheets

U.S. PATENT DOCUMENTS

| | | |
|---|---|---|
| 3,635,215 A | 1/1972 | Shea et al. |
| 3,657,744 A | 4/1972 | Ersek |
| 3,771,526 A | 11/1973 | Rudle |
| 3,868,956 A | 3/1975 | Alfidi et al. |
| 3,993,078 A | 11/1976 | Bergentz et al. |
| 4,078,167 A | 3/1978 | Banas et al. |
| 4,127,761 A | 11/1978 | Pauley et al. |
| 4,130,904 A | 12/1978 | Whalen |
| 4,140,126 A | 2/1979 | Choudhury |
| 4,141,364 A | 2/1979 | Schultze |
| 4,164,045 A | 8/1979 | Bokros et al. |
| 4,214,587 A | 7/1980 | Sakura, Jr. |
| 4,300,244 A | 11/1981 | Bokros |
| 4,313,231 A | 2/1982 | Koyamada |
| 4,319,363 A | 3/1982 | Ketharanathan |
| 4,425,908 A | 1/1984 | Simon |
| 4,441,215 A | 4/1984 | Kaster |
| 4,470,407 A | 9/1984 | Hussein |
| 4,501,264 A | 2/1985 | Rockey |
| 4,503,569 A | 3/1985 | Dotter |
| 4,512,338 A | 4/1985 | Balko et al. |
| 4,535,770 A | 8/1985 | Lemole |
| 4,550,447 A | 11/1985 | Seiler, Jr. et al. |
| 4,553,545 A | 11/1985 | Maass et al. |
| 4,560,374 A | 12/1985 | Hammerslag |
| 4,580,568 A | 4/1986 | Gianturco |
| 4,597,389 A | 7/1986 | Ibrahim et al. |
| 4,647,416 A | 3/1987 | Seiler, Jr. et al. |
| 4,649,922 A | 3/1987 | Wiktor |
| 4,655,771 A | 4/1987 | Wallsten |
| 4,655,776 A | 4/1987 | Lesinski |
| 4,665,906 A | 5/1987 | Jarvis |
| 4,665,918 A | 5/1987 | Garza et al. |
| 4,681,110 A | 7/1987 | Wiktor |
| 4,693,721 A | 9/1987 | Ducheyne |
| 4,733,665 A | 3/1988 | Palmaz |
| 4,739,762 A | 4/1988 | Palmaz |
| 4,740,207 A | 4/1988 | Kreamer |
| 4,760,849 A | 8/1988 | Kropf |
| 4,762,128 A | 8/1988 | Rosenbluth |
| 4,768,507 A | 9/1988 | Fischell et al. |
| 4,769,029 A | 9/1988 | Patel |
| 4,771,773 A | 9/1988 | Kropf |
| 4,776,337 A | 10/1988 | Palmaz |
| 4,787,899 A | 11/1988 | Lazarus |
| 4,795,458 A | 1/1989 | Regan |
| 4,795,465 A | 1/1989 | Marten |
| 4,800,882 A | 1/1989 | Gianturco |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,851,009 A | 7/1989 | Pinchuk |
| 4,856,516 A | 8/1989 | Hillstead |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor |
| 4,913,141 A | 4/1990 | Hillstead |
| 4,922,905 A | 5/1990 | Strecker |
| 4,950,227 A | 8/1990 | Savin et al. |
| 4,950,258 A | 8/1990 | Kawai et al. |
| 4,994,071 A | 2/1991 | MacGregor |
| 5,015,253 A | 5/1991 | MacGregor |
| 5,019,090 A | 5/1991 | Pinchuk |
| 5,035,706 A | 7/1991 | Gianturco et al. |
| 5,037,392 A | 8/1991 | Hillstead |
| 5,059,211 A | 10/1991 | Stack et al. |
| 5,064,435 A | 11/1991 | Porter |
| 5,071,407 A | 12/1991 | Termin et al. |
| 5,089,005 A | 2/1992 | Harada |
| 5,092,877 A | 3/1992 | Pinchuk |
| 5,102,417 A | 4/1992 | Palmaz |
| 5,104,399 A | 4/1992 | Lazarus |
| 5,104,404 A | 4/1992 | Wolff |
| 5,108,415 A | 4/1992 | Pinchuk et al. |
| 5,108,417 A | 4/1992 | Sawyer |
| 5,122,154 A | 6/1992 | Rhodes |
| 5,133,732 A | 7/1992 | Wiktor |
| 5,135,536 A | 8/1992 | Hillstead |
| 5,139,480 A | 8/1992 | Hickle et al. |
| 5,147,385 A | 9/1992 | Beck et al. |
| 5,147,400 A | 9/1992 | Kaplan et al. |
| 5,158,548 A | 10/1992 | Lau et al. |
| 5,163,952 A | 11/1992 | Froix |
| 5,195,984 A | 3/1993 | Schatz |
| 5,197,978 A | 3/1993 | Hess |
| 5,217,483 A | 6/1993 | Tower |
| 5,226,913 A | 7/1993 | Pinchuk |
| 5,282,823 A | 2/1994 | Schwartz et al. |
| 5,282,824 A | 2/1994 | Gianturco |
| 5,292,331 A | 3/1994 | Boneau |
| 5,304,200 A | 4/1994 | Spaulding |
| 5,344,425 A | 9/1994 | Sawyer |
| 5,354,308 A | 10/1994 | Simon et al. |
| 5,354,309 A | 10/1994 | Schnepp-Pesch et al. |
| 5,356,423 A | 10/1994 | Tibon et al. |
| 5,383,892 A | 1/1995 | Cardon et al. |
| 5,389,106 A | 2/1995 | Tower .................. 606/198 |
| 5,405,377 A | 4/1995 | Cragg |
| 5,449,373 A | 9/1995 | Pinchasik et al. |
| 5,527,354 A | 6/1996 | Fontaine et al. |
| 5,545,210 A | 8/1996 | Hess et al. |
| 5,549,663 A | 8/1996 | Cottone, Jr. |
| 5,554,181 A | 9/1996 | Das |
| 5,591,197 A | 1/1997 | Orth et al. |
| 5,630,829 A | 5/1997 | Lauterjung |
| 5,643,312 A | 7/1997 | Fischell et al. |
| 5,653,727 A | 8/1997 | Wiktor |
| 5,707,386 A | 1/1998 | Schnepp-Pesch et al. |
| 5,725,572 A * | 3/1998 | Lam et al. ............... 623/1.16 |
| 5,800,521 A * | 9/1998 | Orth ....................... 606/195 |
| 5,935,161 A * | 8/1999 | Robinson et al. ........ 606/195 |
| 5,954,743 A * | 9/1999 | Jang ....................... 623/1.15 |
| 5,972,018 A * | 10/1999 | Israel et al. ............. 623/1.15 |
| 6,090,127 A * | 7/2000 | Globerman ............. 606/194 |
| 6,129,755 A * | 10/2000 | Mathis et al. ........... 623/1.15 |
| 6,156,052 A * | 12/2000 | Richter et al. .......... 606/191 |

OTHER PUBLICATIONS

Improved Dilation Catheter Balloons, by Stanley B. Levy, Ph.D., *Journal of Clinical Engineering*, vol. 11, No. 4, Jul.–Aug. 1986, pp. 291–296.

Self–expanding Stainless Steel Biliary Stents[1], By Harold G. Coons, MD, *Radiology 1989*, vol. 170, No. 3, Part 2, pp. 979–983.

Technical Note Entitled Modifications of Gianturco Expandable Wire Stents, By Barry T. Uchida et al., *AJR*, vol. 150, May 1988, pp. 1185–1187.

Brochure from Cook Incorporated regarding Gianturco–Rosch Biliary Z–Stents™.

Expandable Biliary Endoprosthesis: An Experimental Study, By Carrasco et al., *AJR*, vol. 145, Dec. 1985, pp. 1279–1282.

Gianturco Expandable Metallic Biliary Stents: Results of a European Clinical Trial[1], By Irving, et al., *Interventional Radiology*, vol. 172, No. 2, Aug. 1989, pp. 321–326.

Tracheobronchial Tree: Expandable Metallic Stents Used in Experimental and Clinical Applications[1], Work In Progress, By Wallace et al., *Radiology*, Feb. 1986, pp. 309–312.

Brochure Entitled *Ave Micro Stent*™, Instructions for Use, By Applied Fascular Engineering, Inc., pp. 1–15.

Brochure Entitled *Micro Stent*™, By Applied Vascular Engineering, Inc.

* cited by examiner

LONGITUDINALLY FLEXIBLE EXPANDABLE STENT

This application is a continuation of Ser. No. 08/511,076 filed Aug. 3, 1995 which is a continuation-in-part of Ser. No. 08/396,569 filed Mar. 1, 1995 and now abandoned.

FIELD OF THE INVENTION

This invention relates to an endoprosthesis device for implantation within a body vessel, typically a blood vessel. More specifically, it relates to a tubular expandable stent of improved longitudinal flexibility.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in the urinary tract and in bile ducts.

Typically, a stent will have an unexpanded (closed) diameter for placement and an expanded (opened) diameter after placement in the vessel or the duct. Some stents are self-expanding and some are expanded mechanically with radial outward force from within the stent, as by inflation of a balloon.

An example of the latter type is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

This invention is directed to stents of all these types when configured so as to be longitudinally flexible as described in detail hereinbelow. Flexibility is a desirable feature in a stent so as to conform to bends in a vessel. Such stents are known n the prior art. Examples are shown in U.S. Pat. No. 4,856,516 to Hillstead; U.S. Pat. No. 5,104,404 to Wolff; U.S. Pat. No. 4,994,071 to MacGregor; U.S. Pat. No. 5,102,417 to Palmaz; U.S. Pat. No. 5,195,984 to Schatz; U.S. Pat. No. 5,135,536 to Hillstead; U.S. Pat. No. 5,354,309 to Shepp-Pesch et al.; EPO Patent Application 0 540 290 A2 to Lau; EPO Patent Application No. 0 364 787 B1 to Schatz, and PCT Application WO 94/17754 (also identified as German Patent Application 43 03 181).

Generally speaking, these kinds of stents are articulated and are usually formed of a plurality of aligned, expandable, relatively inflexible, circular segments which are interconnected by flexible elements to form a generally tubular body which is capable of a degree of articulation or bending. Unfortunately, a problem with such stents is that binding, overlapping or interference can occur between adjacent segments on the inside of a bend due to the segments moving toward each other and into contact or on the outside of a bend the segments can move away from each other, leaving large gaps. This can lead to improper vessel support, vessel trauma, flow disturbance, kinking, balloon burst during expansion, and difficult recross for devices to be installed through already implanted devices and to unsupported regions of vessel.

A diamond configuration with diagonal connections between each and every diamond of each segment is also known but such closed configurations lack flexibility.

It is an object of this invention to provide a longitudinally flexible stent of open configuration that avoids these problems and exhibits improved flexibility (radially and longitudinally) in the stent body segments thereof rather than in flexible joints between the segments.

SUMMARY OF THE INVENTION

To this end, the invention provides a tubular expandable stent, comprising: a plurality of cylindrical shaped open cylindrical segments aligned on a common longitudinal axis to define a generally tubular stent body, each segment being defined by a member formed in an undulating flexible pattern of interconnected substantially parallel struts with pairs thereof having alternating interconnecting end portions to define the periphery of the expandable stent segment, and in which the connected end portions of paired struts in each segment, before the stent is expanded, are positioned substantially opposite to connected end portions of paired struts in adjacent segments. The segments are interconnected by a plurality of interconnecting elements extending from some of the connected end portions on one segment to some of the connected end portions on adjacent segments in such a manner that there are three or more legs between points of connection from one side of each segment to its other side. Additionally, the connecting elements extend angularly from connecting end portion of one segment to connecting end portion of an adjacent segment, not to an opposite connecting end portion on an adjacent segment, whereby upon expansion of the stent the adjacent segments are displaced relative to each other about the periphery of the stent body to accommodate flexing of the stent within paired struts without interference between adjacent segments, rather than by means of articulating flexible connectors between segments. As a result, the connectors between the segments are not intended to flex or bend under normal use.

BEST MODE DESCRIPTION OF THE INVENTION

Figure 1:
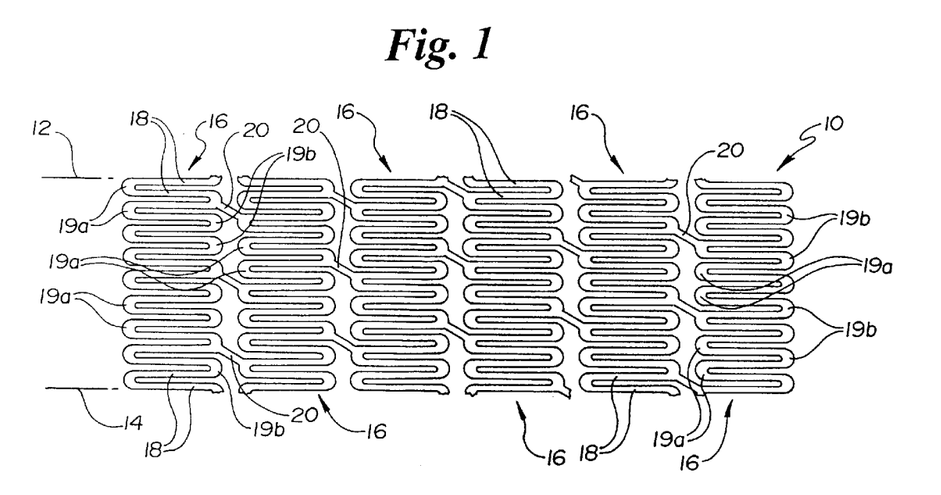
FIG. 1 shows a flat view of an unexpanded stent configuration according to the invention.
Figure 2:
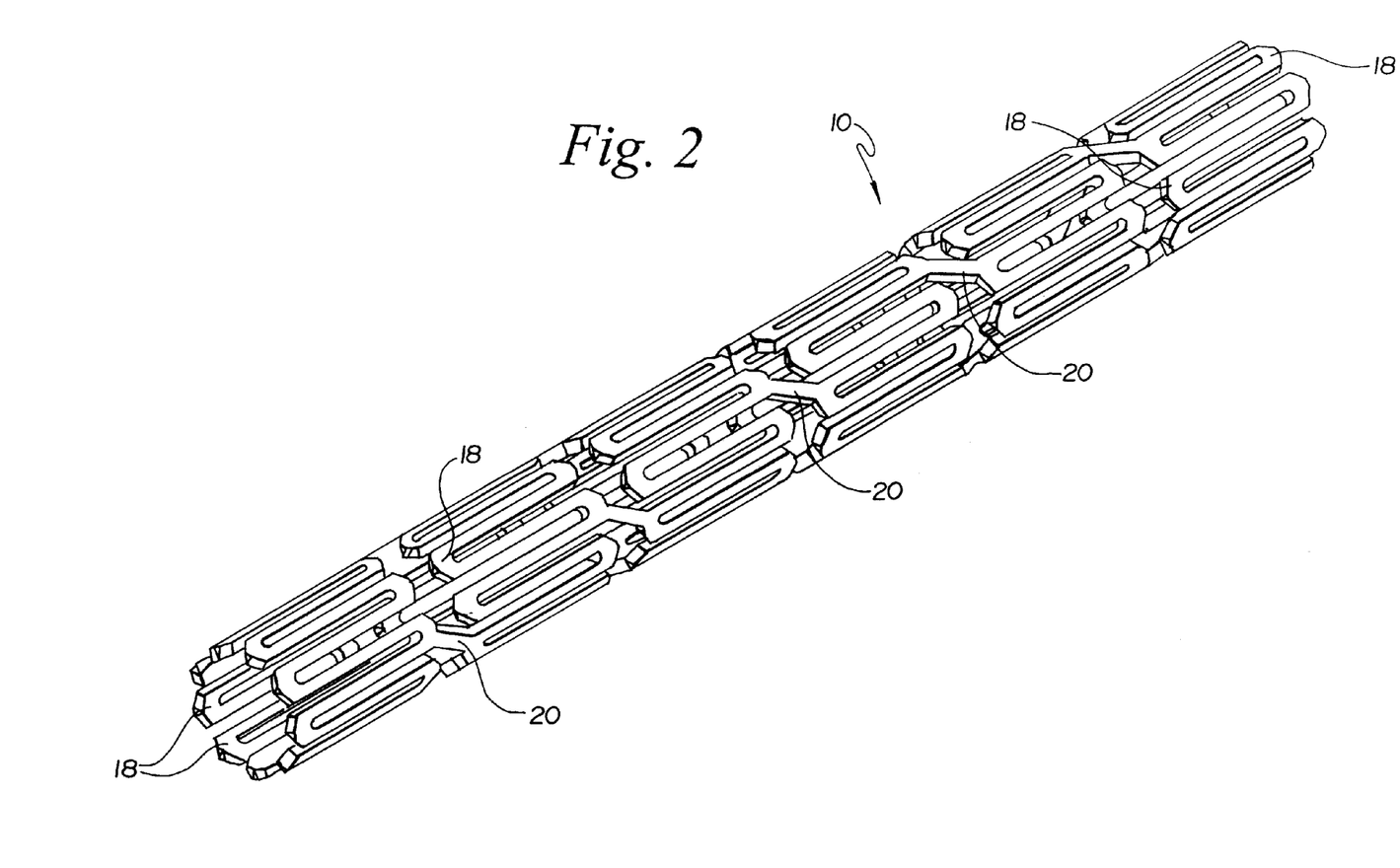
FIG. 2 shows the pattern of FIG. 1 in a tubular, unexpanded stent.

Turning to the Figures, FIG. 1 and FIG. 2 show a fragmentary flat view of an unexpanded stent configuration and the actual tubular stent (unexpanded), respectively. That is, the stent is shown for clarity in FIG. 1 in the flat and may be made from a flat pattern 10 (FIG. 1) which is formed into a tubular shape by rolling the pattern so as to bring edges 12 and 14 together (FIG. 1). The edges may then joined as by welding or the like to provide a configuration such as that shown in FIG. 2.

The configuration can be seen in these Figures to be made up of a plurality of adjacent segments generally indicated at 16, each of which is formed in an undulating flexible pattern of substantially parallel struts 18. Pairs of struts are interconnected at alternating end portions 19a and 19b. As is seen in FIG. 1, the interconnecting end portions 19b of one segment are positioned opposite interconnecting end portions 19a of adjacent segments. The end portions as shown are generally elliptical but may be rounded or square or pointed or the like. Any configuration of end portions is acceptable so long as it provides an undulating pattern, as shown. When the flat form 10 is formed into an unexpanded tube as shown in FIG. 2, the segments are cylindrical but the end portions 19 of adjacent segments remain in an opposed position relative to each other.

A more preferred method of manufacture begins with a thin walled tube which is then laser cut to provide the desired configuration. It may also be chemically etched or EDM'd (electrical discharge machined) to form an appropriate configuration.

Figure 5:
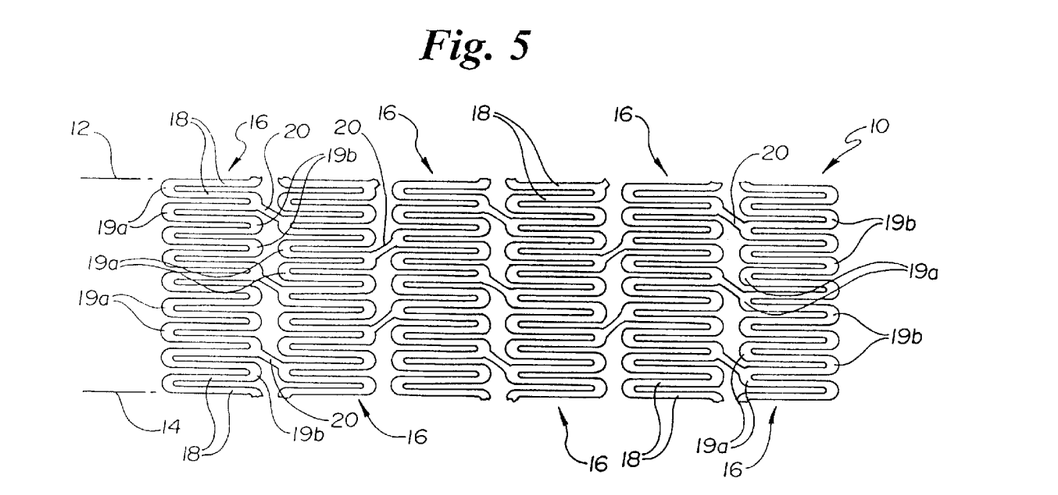
FIG. 5 shows a flat view of an alternative unexpanded stent configuration according to the invention.

Interconnecting elements 20 extend from one end portion 19 of one segment 16 to another end portion 19 of another adjacent segment 16 but not to an oppositely positioned end portion 19 of an adjacent segment 16. There are at least three struts included between the points on each side of a segment 16 at which an interconnecting element 20 contacts an end portion 19. This results in the interconnecting elements 20 extending in an angular direction between segments around the periphery of the tubular stent. Interconnecting elements 20 are preferably of the same length but may vary from one segment to the other. Also, the diagonal direction may reverse from one segment to another extending upwardly in one case and downwardly in another, as shown in FIG. 5 although all connecting elements between any pair of segments are substantially parallel. FIG. 1, for example shows them extending downwardly, right to left. Upwardly would extend up left to right in this configuration.

Figure 3:
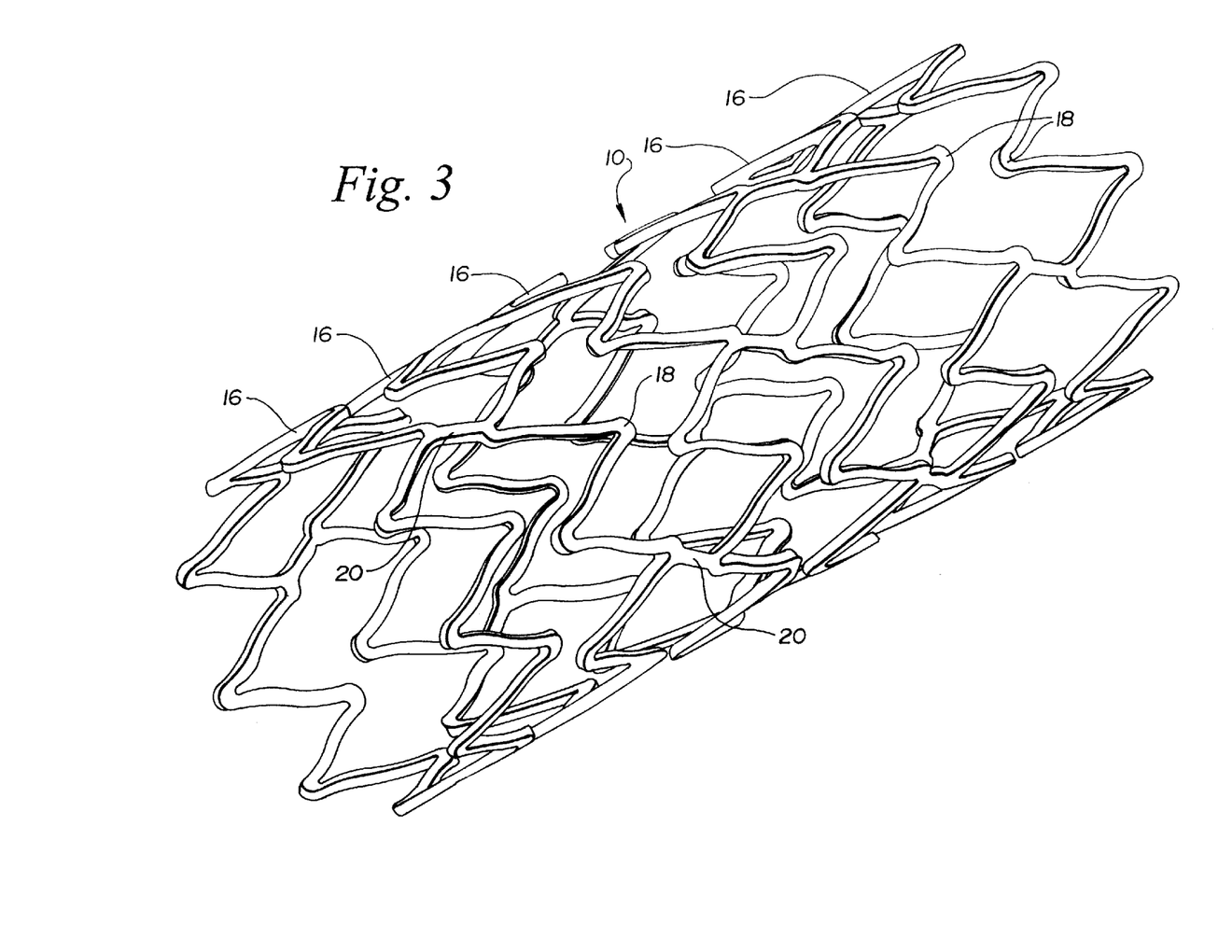
FIG. 3 shows an expanded stent of the configuration shown in FIG. 1.

As a result of this angular extension of the interconnecting elements 20 between adjacent segments and loops, upon expansion of the stent as seen in FIG. 3, the closest adjacent end portions 19 between segments 16 are displaced from each other and are no longer opposite each other so as to minimize the possibility of binding or overlapping between segments, i.e., pinching.

The number of interconnecting elements 20 may vary depending on circumstances in any particular instance. Three per segment are satisfactory for the configuration shown and at least three will be used typically.

Figure 4:
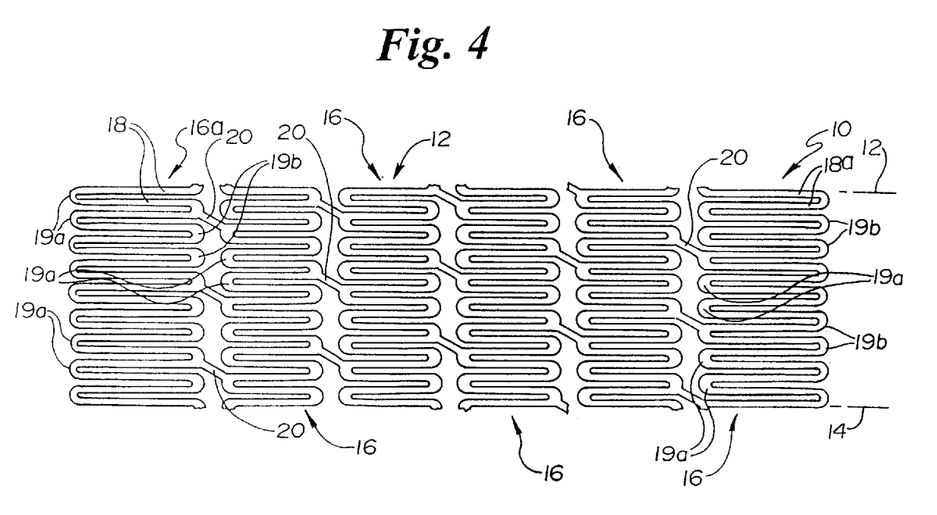
FIG. 4 shows a flat view of an alternate unexpanded stent configuration according to the invention.

The alternate design shown in FIG. 4 includes longer struts 18a in the two end segments 16a than in the intermediate segments 16. This allows the end segments (16a) to have less compression resistance than the intermediate segments (16), providing a more gradual transition from the native vessel to the support structure of the stent. Otherwise, the configuration is the same as that shown in FIG. 1.

As already indicated, this invention is applicable to self-expanding configurations, mechanically expandable configurations and to a wide variety of materials, including both metal and plastic and any other material capable of functioning as an expandable stent. For example, the stent may be of metal wire or ribbon such as tantalum, stainless steel or the like. It may be thin-walled. It may be of shape memory alloy such as Nitinol or the like, etc.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A tubular, flexible, self-expandable stent comprising:
   1) a plurality of cylindrically shaped segments which are interconnected,
      one of the cylindrically shaped segments being an intermediate cylindrically shaped segment having a proximal end and a distal end,
      one of the cylindrically shaped segments being a proximal cylindrically shaped segment having a proximal end and a distal end located adjacent the proximal end of the intermediate cylindrically shaped segment and
      one of the cylindrically shaped segments being a distal cylindrically shaped segment having a distal end and a proximal end located adjacent the distal end of the intermediate cylindrically shaped segment,
      each cylindrically shaped segment being defined by an undulating pattern of interconnected struts, each strut having a proximal end and a distal end, each strut adjacent a first strut and a second strut, the strut and the first strut interconnected only at their distal ends, the strut and the second strut interconnected only at their proximal ends, and
   2) a plurality of interconnecting elements including proximal interconnecting elements and distal interconnecting elements, each interconnecting element having a proximal end and a distal end, the proximal end of the interconnecting element circumferentially and longitudinally offset from the distal end of the interconnecting element, the interconnecting elements shorter in length than the cylindrically shaped segments,
      each proximal interconnecting element extending proximally from an interconnected proximal end of adjacent struts on the intermediate cylindrically shaped segment to an interconnected distal end of adjacent struts on the proximal cylindrically shaped segment,
      each distal interconnecting element extending distally from an interconnected distal end of adjacent struts on the intermediate cylindrically shaped segment to an interconnected proximal end of adjacent struts on the distal cylindrically shaped segment,
      the interconnecting elements extending at an oblique angle relative to the longitudinal axis, a minimum length pathway of at least three interconnected circumferentially adjacent struts on the intermediate cylindrically shaped segment extending between the distal ends of the proximal interconnecting elements and the proximal ends of the distal interconnecting elements,
   wherein flexing of the stent occurs substantially in the cylindrically shaped segments.

2. The stent of claim 1 formed of a shape memory metal.

3. The stent of claim 2 formed of nitinol.

4. The stent of claim 1 wherein each interconnecting element extends from a side of an interconnected end of adjacent struts on one cylindrically shaped segment to a side of an interconnected end of adjacent struts on an adjacent cylindrically shaped segment.

5. The stent of claim 1 wherein circumferentially adjacent interconnecting elements are separated by six struts.

6. The stent of claim 1 wherein there are at least three interconnecting elements extending between any two adjacent cylindrically shaped segments.

7. The stent of claim 1 constructed and arranged such that upon expansion of the stent, connected ends of adjacent struts in the proximal cylindrically shaped segment are circumferentially displaced relative to connected ends of adjacent struts in the intermediate cylindrically shaped segment and connected ends of adjacent struts in the intermediate cylindrically shaped segment are circumferentially displaced relative to connected ends of adjacent struts in the distal cylindrically shaped segment to accommodate longitudinal flexing of the stent within the cylindrically shaped segments and without interference between adjacent cylindrically shaped segments.

8. A tubular, flexible, self-expandable stent made of nitinol, the stent comprising:
1) a plurality of cylindrically shaped segments which are interconnected,
   one of the cylindrically shaped segments being an intermediate cylindrically shaped segment having a proximal end and a distal end,
   one of the cylindrically shaped segments being a proximal cylindrically shaped segment having a proximal end and a distal end located adjacent the proximal end of the intermediate cylindrically shaped segment and
   one of the cylindrically shaped segments being a distal cylindrically shaped segment having a distal end and a proximal end located adjacent the distal end of the intermediate cylindrically shaped segment,
   each cylindrically shaped segment being defined by an undulating pattern of interconnected struts, each strut having a proximal end and a distal end, each strut adjacent a first strut and a second strut, the strut and the first strut interconnected only at their distal ends, the strut and the second strut interconnected only at their proximal ends, and
2) a plurality of interconnecting elements including proximal interconnecting elements and distal interconnecting elements, each interconnecting element having a proximal end and a distal end, the proximal end of the interconnecting element circumferentially and longitudinally offset from the distal end of the interconnecting element, the interconnecting elements shorter in length than the cylindrically shaped segments,
   each proximal interconnecting element extending proximally from an interconnected proximal end of adjacent struts on the intermediate cylindrically shaped segment to an interconnected distal end of adjacent struts on the proximal cylindrically shaped segment,
   each distal interconnecting element extending distally from an interconnected distal end of adjacent struts on the intermediate cylindrically shaped segment to an interconnected proximal end of adjacent struts on the distal cylindrically shaped segment,
   a minimum length pathway of at least three interconnected circumferentially adjacent struts on the intermediate cylindrically shaped segment extending between the distal ends of the proximal interconnecting elements and the proximal ends of the distal interconnecting elements,
wherein upon expansion of the stent interconnected ends of adjacent struts in the proximal cylindrically shaped segment are circumferentially displaced relative to interconnected ends of adjacent struts in the intermediate cylindrically shaped segment and interconnected ends of adjacent struts in the intermediate cylindrically shaped segment are circumferentially displaced relative to interconnected ends of adjacent struts in the distal cylindrically shaped segment to accommodate longitudinal flexing of the stent substantially within the cylindrically shaped segments without substantial flexing of the interconnecting elements and without interference between adjacent cylindrically shaped segments.

9. The stent of claim 8 wherein each interconnecting element extends from a side of an interconnected end of adjacent struts on one cylindrically shaped segment to a side of an interconnected end of adjacent struts on an adjacent cylindrically shaped segment.

10. The stent of claim 8 wherein circumferentially adjacent interconnecting elements are separated by six struts.

11. The stent of claim 8 wherein there are at least three interconnecting elements extending between any two adjacent cylindrically shaped segments.

12. A tubular, flexible, self-expandable stent comprising:
1) a plurality of cylindrically shaped segments which are interconnected,
   one of the cylindrically shaped segments being an intermediate cylindrically shaped segment having a proximal end and a distal end,
   one of the cylindrically shaped segments being a proximal cylindrically shaped segment having a proximal end and a distal end located adjacent the proximal end of the intermediate cylindrically shaped segment and
   one of the cylindrically shaped segments being a distal cylindrically shaped segment having a distal end and a proximal end located adjacent the distal end of the intermediate cylindrically shaped segment,
   each cylindrically shaped segment being defined by an undulating pattern of interconnected struts, each strut having a proximal end and a distal end, each strut adjacent a first strut and a second strut, the strut and the first strut interconnected only at their distal ends, the strut and the second strut interconnected only at their proximal ends, and
2) a plurality of interconnecting elements including proximal interconnecting elements and distal interconnecting elements, each interconnecting element having a proximal end and a distal end, the proximal end of the interconnecting element circumferentially and longitudinally offset from the distal end of the interconnecting element, the interconnecting elements shorter in length than the cylindrically shaped segments,
   each proximal interconnecting element extending proximally from an interconnected proximal end of adjacent struts on the intermediate cylindrically shaped segment to an interconnected distal end of adjacent struts on the proximal cylindrically shaped segment,
   each distal interconnecting element extending distally from an interconnected distal end of adjacent struts on the intermediate cylindrically shaped segment to an interconnected proximal end of adjacent struts on the distal cylindrically shaped segment,
   the interconnecting elements extending at an oblique angle relative to the longitudinal axis, a minimum length pathway of at least three interconnected circumferentially adjacent struts on the intermediate cylindrically shaped segment extending between the distal ends of the proximal interconnecting elements and the proximal ends of the distal interconnecting elements, at least three interconnecting elements extending between any two adjacent cylindrically shaped segments, wherein upon expansion of the stent interconnected ends of adjacent struts in the proximal cylindrically shaped segment are displaced circumferentially relative to interconnected ends of adjacent struts in the intermediate cylindrically shaped segment and interconnected ends of adjacent struts in the intermediate cylindrically shaped segment are circumferentially displaced relative to interconnected ends of adjacent struts in the distal cylindrically shaped segment to accommodate longitudinal flexing of the stent substantially within the cylindrically shaped segments and without interference between adjacent cylindrically shaped segments.

13. The stent of claim 12 wherein the direction of the interconnecting elements reverses between adjacent pairs of interconnected segments.

14. The stent of claim 12 wherein circumferentially adjacent interconnecting elements are separated by six struts.

15. The stent of claim 1 wherein the direction of the interconnecting elements reverses between adjacent pairs of interconnected cylindrically shaped segments.

16. The stent of claim 8 wherein the direction of the interconnecting elements reverses between adjacent pairs of interconnected cylindrically shaped segments.

17. A tubular, flexible, self-expandable stent comprising:
1) a plurality of cylindrically shaped segments which are interconnected including
   a first cylindrically shaped segment defined by an undulating pattern of interconnected first struts, each first strut having a proximal end and a distal end, first struts which are circumferentially adjacent one another and connected at the proximal ends of the first struts forming first troughs, first struts which are circumferentially adjacent one another and connected at the distal ends of the first struts forming first peaks, the first troughs and the first peaks alternating with one another and circumferentially offset from one another about the first cylindrically shaped segment,
   a second cylindrically shaped segment defined by an undulating pattern of interconnected second struts, each second strut having a proximal end and a distal end, second struts which are circumferentially adjacent one another and connected at the proximal ends of the second struts forming second troughs, second struts which are circumferentially adjacent one another and connected at the distal ends of the second struts forming second peaks, the second troughs and the second peaks alternating with one another and circumferentially offset from one another about the second cylindrically shaped segment,
   a third cylindrically shaped segment defined by an undulating pattern of interconnected third struts, each third strut having a proximal end and a distal end, third struts which are circumferentially adjacent one another and connected at the proximal ends of the third struts forming third troughs, third struts which are circumferentially adjacent one another and connected at the distal ends of the third struts forming third peaks, the third troughs and the third peaks alternating with one another and circumferentially offset from one another about the third cylindrically shaped segment, and
2) a plurality of first connectors connecting the first cylindrically shaped segment and the second cylindrically shaped segment, each first connector having a first end and a second end circumferentially and longitudinally offset from the first end, each first connector extending from one of the first peaks to one of the second troughs, each first connector extending at an oblique angle relative to the longitudinal axis, first connectors which are adjacent one another separated by six first struts, the first connectors shorter in length than the first and second cylindrically shaped segments,
   a plurality of second connectors connecting the second cylindrically shaped segment and the third cylindrically shaped segment, each second connector having a first end and a second end circumferentially and longitudinally offset from the first end, each second connector extending from one of the second peaks to one of the third troughs, each second connector extending at an oblique angle relative to the longitudinal axis, second connectors which are adjacent one another separated by six second struts, the second connectors shorter in length than the second and third cylindrically shaped segments,
   the second end of each first connector separated from the first end of a second connector which is nearest to it by at least three second struts,
   whereby flexing of the stent occurs substantially in the cylindrically shaped segments.

18. The stent of claim 17 formed of a shape memory metal.

19. The stent of claim 18 formed of nitinol.

20. The stent of claim 17, each first peak having a first side, a second side and a middle portion between the first and second sides, each second trough having a first side, a second side and a middle portion between the first and second sides, each second peak having a first side, a second side and a middle portion between the first and second sides, and each third trough having a first side, a second side and a middle portion between the first and second sides,
   wherein each first connector extends from the first side of one of the first peaks to the second side of one of the second troughs and each second connector extends from the first side of one of the second peaks to the second side of one of the third troughs.

21. The stent of claim 17, each first connector having a longitudinal axis and each second connector having a longitudinal axis, the longitudinal axis of each first connector intersecting the longitudinal axis of the second connector nearest to the first connector at an angle, the angle bisected by an imaginary line parallel to the longitudinal axis of the stent.

22. The stent of claim 17 wherein there are at least three first connectors and at least three second connectors.

23. The stent of claim 17 constructed and arranged such that upon expansion of the stent, the first peaks are circumferentially displaced relative to the second troughs and the second peaks are circumferentially displaced relative to the third troughs to accommodate longitudinal flexing of the stent within the cylindrically shaped segments and without interference between adjacent cylindrically shaped segments.

24. The stent of claim 17 wherein the direction of the second connectors is reversed relative to the direction of the first connectors.

25. The stent of claim 17 wherein the first cylindrically shaped segment has a first amplitude characterized by the longitudinal distance between the first peaks and the first troughs and the second cylindrically shaped segment has a second amplitude characterized by the longitudinal distance between the second peaks and the second troughs, the first amplitude different from the second amplitude.

26. The stent of claim 17 wherein the first connectors are longer than the second connectors.

27. A stent having a proximal end and a distal end and a longitudinal axis, the stent comprising:
1) a plurality of undulating cylindrical segments including
   a first undulating cylindrical segment comprising a plurality of alternating first peaks and first troughs, the first peaks pointing toward the distal end of the stent, the first troughs pointing toward the proximal end of the stent;
   a second undulating cylindrical segment comprising a plurality of alternating second peaks and second troughs, the second peaks pointing toward the distal end of the stent, the second troughs pointing toward the proximal end of the stent;
   a third undulating cylindrical segment comprising a plurality of alternating third peaks and third troughs, the third peaks pointing toward the distal end of the stent, the third troughs pointing toward the proximal end of the stent;
2) a plurality of connectors including
   a plurality of first connectors connecting the first undulating cylindrical segment and the second undulating cylindrical segment, each first connector having a proximal end and a distal end circumferentially and longitudinally displaced from the proximal end, the proximal end extending from one of the first peaks, the distal end extending from one of the second troughs, the first connectors extending from every third first peak and every third second trough, the first connectors shorter in length than the first undulating cylindrical segment and the second undulating cylindrical segment,
   a plurality of second connectors connecting the second undulating cylindrical segment and the third undulating cylindrical segment, each second connector having a proximal end and a distal end circumferentially and longitudinally displaced from the proximal end, the proximal end extending from one of the second peaks, the distal end extending from one of the third troughs, the second connectors extending from every third second peak and every third third trough, the second connectors shorter in length than the second undulating cylindrical segment and the third undulating cylindrical segment, each first connector separated from a second connector which is nearest to it by at least one second peak and one second trough,
wherein flexing of the stent occurs substantially in the undulating cylindrical segments.

28. The stent of claim 27 formed of a shape memory metal.

29. The stent of claim 28 formed of nitinol.

30. The stent of claim 27 wherein there are at least three first connectors connecting the first and second undulating cylindrical segments.

31. The stent of claim 27 constructed and arranged such that upon expansion of the stent, peaks of undulating cylindrical segments are circumferentially displaced relative to troughs of adjacent undulating cylindrical segments to accommodate longitudinal flexing of the stent within the cylindrically shaped segments and without interference between adjacent cylindrically shaped segments.

32. The stent of claim 31 wherein the connectors are substantially linear.

33. The stent of claim 32 wherein the connectors extend diagonally relative to the longitudinal axis of the stent.

34. The stent of claim 27 each first peak having a first side, a second side and a middle portion between the first and second sides, each second trough having a first side, a second side and a middle portion between the first and second sides, each second peak having a first side, a second side and a middle portion between the first and second sides, and each third trough having a first side, a second side and a middle portion between the first and second sides,
wherein each first connector extends from the first side of one of the first peaks to the second side of one of the second troughs and each second connector extends from the first side of one of the second peaks to the second side of one of the third troughs.

35. The stent of claim 27, each first connector having a longitudinal axis and each second connector having a longitudinal axis, the longitudinal axis of each first connector intersecting the longitudinal axis of the second connector nearest to the first connector at an angle, the angle bisected by an imaginary line parallel to the longitudinal axis of the stent.

36. The stent of claim 27 wherein the direction of the second connectors is reversed relative to the direction of the first connectors.

37. The stent of claim 27 wherein the first undulating cylindrical segment has a first amplitude characterized by the longitudinal distance between the first peaks and the first troughs and the second undulating cylindrical segment has a second amplitude characterized by the longitudinal distance between the second peaks and the second troughs, the first amplitude different from the second amplitude.

38. The stent of claim 27 wherein the first connectors are characterized by a first length and the second connectors are characterized by a second length, the first length different from the second length.

39. A stent having a proximal end and a distal end, the stent comprising:
1) a plurality of undulating cylindrical segments including
   a first undulating cylindrical segment comprising a plurality of alternating first peaks and first troughs, the first peaks pointing toward the distal end of the stent, the first troughs pointing toward the proximal end of the stent;
   a second undulating cylindrical segment comprising a plurality of alternating second peaks and second troughs, the second peaks pointing toward the distal end of the stent, the second troughs pointing toward the proximal end of the stent;
   a third undulating cylindrical segment comprising a plurality of alternating third peaks and third troughs, the third peaks pointing toward the distal end of the stent, the third troughs pointing toward the proximal end of the stent; and
2) a plurality of connectors including
   a plurality of first connectors connecting the first undulating cylindrical segment and the second undulating cylindrical segment, each first connector having a proximal end and a distal end circumferentially and longitudinally displaced from the proximal end, the proximal end extending from one of the first peaks, the distal end extending from one of the second troughs, the first connectors extending from every third first peak and every third second trough, the first connectors shorter in length than the first undulating cylindrical segment and the second undulating cylindrical segment,
   a plurality of second connectors connecting the second undulating cylindrical segment and the third undulating cylindrical segment, each second connector having a proximal end and a distal end circumferentially and longitudinally displaced from the proximal end, the proximal end extending from one of the second peaks, the distal end extending from one of the third troughs, the second connectors extending from every third second peak and every third third trough, the second connectors shorter in length than the second undulating cylindrical segment and the third undulating cylindrical segment, each first connector separated from a second connector which is nearest to it by at least one second peak and one second trough, wherein upon expansion of the stent the first peaks are circumferentially displaced relative to the second troughs and the second peaks are circumferentially displaced relative to the third troughs to accommodate longitudinal flexing of the stent substantially within the undulating cylindrical segments without substantial flexing of the connectors, without interference between the first and second undulating cylindrical segments and without interference between the second and third undulating cylindrical segments.

40. The stent of claim 1 wherein in interconnecting elements are of a shorter length than the struts.

41. The stent of claim 17 wherein the first connectors are shorter than the second connectors.

42. A stent comprising:
1) a plurality of cylindrically shaped segments which are interconnected,
    one of the cylindrically shaped segments being an intermediate cylindrically shaped segment having a proximal end and a distal end,
    one of the cylindrically shaped segments being a proximal cylindrically shaped segment having a proximal end and a distal end located adjacent the proximal end of the intermediate cylindrically shaped segment and
    one of the cylindrically shaped segments being a distal cylindrically shaped segment having a distal end and a proximal end located adjacent the distal end of the intermediate cylindrically shaped segment,
    each cylindrically shaped segment being defined by an undulating pattern of interconnected struts, each strut having a proximal end and a distal end, each strut adjacent a first strut and a second strut, the strut and the first strut interconnected only at their distal ends, the strut and the second strut interconnected only at their proximal ends, and
2) a plurality of interconnecting elements including proximal interconnecting elements and distal interconnecting elements, each interconnecting element having a proximal end and a distal end, the proximal end of the interconnecting element circumferentially and longitudinally offset from the distal end of the interconnecting element, the interconnecting elements shorter in length than the cylindrically shaped segments,
    each proximal interconnecting element extending proximally from an interconnected proximal end of adjacent struts on the intermediate cylindrically shaped segment to an interconnected distal end of adjacent struts on the proximal cylindrically shaped segment,
    each distal interconnecting element extending distally from an interconnected distal end of adjacent struts on the intermediate cylindrically shaped segment to an interconnected proximal end of adjacent struts on the distal cylindrically shaped segment,
    the interconnecting elements non-parallel to the longitudinal axis, a minimum length pathway of at least three interconnected circumferentially adjacent struts on the intermediate cylindrically shaped segment extending between the distal ends of the proximal interconnecting elements and the proximal ends of the distal interconnecting elements, wherein flexing of the stent occurs substantially in the cylindrically shaped segments.

43. The stent of claim 42 wherein circumferentially adjacent interconnecting elements are separated by six struts.

44. A stent comprising:
1) a plurality of cylindrically shaped segments which are interconnected,
    one of the cylindrically shaped segments being an intermediate cylindrically shaped segment having a proximal end and a distal end,
    one of the cylindrically shaped segments being a proximal cylindrically shaped segment having a proximal end and a distal end located adjacent the proximal end of the intermediate cylindrically shaped segment and
    one of the cylindrically shaped segments being a distal cylindrically shaped segment having a distal end and a proximal end located adjacent the distal end of the intermediate cylindrically shaped segment,
    each cylindrically shaped segment being defined by an undulating pattern of interconnected struts, each strut having a proximal end and a distal end, each strut adjacent a first strut and a second strut, the strut and the first strut interconnected only at their distal ends, the strut and the second strut interconnected only at their proximal ends, and
2) a plurality of interconnecting elements including proximal interconnecting elements and distal interconnecting elements, each interconnecting element having a proximal end and a distal end, the proximal end of the interconnecting element circumferentially and longitudinally offset from the distal end of the interconnecting element, the interconnecting elements shorter in length than the cylindrically shaped segments,
    each proximal interconnecting element extending proximally from an interconnected proximal end of adjacent struts on the intermediate cylindrically shaped segment to an interconnected distal end of adjacent struts on the proximal cylindrically shaped segment,
    each distal interconnecting element extending distally from an interconnected distal end of adjacent struts on the intermediate cylindrically shaped segment to an interconnected proximal end of adjacent struts on the distal cylindrically shaped segment,
    the interconnecting elements non-parallel to the longitudinal axis, a minimum length pathway of at least three interconnected circumferentially adjacent struts on the intermediate cylindrically shaped segment extending between the distal ends of the proximal interconnecting elements and the proximal ends of the distal interconnecting elements, at least three interconnecting elements extending between any two adjacent cylindrically shaped segments, wherein upon expansion of the stent interconnected ends of adjacent struts in the proximal cylindrically shaped segment are displaced circumferentially relative to interconnected ends of adjacent struts in the intermediate cylindrically shaped segment and interconnected ends of adjacent struts in the intermediate cylindrically shaped segment are circumferentially displaced relative to interconnected ends of adjacent struts in the distal cylindrically shaped segment to accommodate longitudinal flexing of the stent substantially within the cylindrically shaped segments and without interference between adjacent cylindrically shaped segments.

45. The stent of claim 44 wherein circumferentially adjacent interconnecting elements are separated by six struts.

\* \* \* \* \*